United States Patent [19]

Krapcho

[11] 4,053,471

[45] Oct. 11, 1977

[54] 4-THIAZOLIDINONE DERIVATIVES

[75] Inventor: John Krapcho, Somerset, N.J.

[73] Assignee: E. R. Squibb & Sons, Inc., Princeton, N.J.

[21] Appl. No.: 740,705

[22] Filed: Nov. 11, 1976

[51] Int. Cl.$^2$ .................. C07D 295/14; C07D 277/14
[52] U.S. Cl. ............................... 544/133; 260/268 H; 260/293.68; 260/306.7 R; 424/248.51; 424/250; 424/267; 424/270
[58] Field of Search ................... 260/247.1 H, 268 H, 260/293.68, 306.7 R

[56] References Cited

U.S. PATENT DOCUMENTS 2,623,048  12/1952  Long et al. ................... 260/306.7 R Primary Examiner—Henry R. Jiles
Assistant Examiner—R. W. Ramsuer Attorney, Agent, or Firm—Lawrence S. Levinson; Merle J. Smith; Donald J. Barrack

[57] ABSTRACT

Compounds having the formula

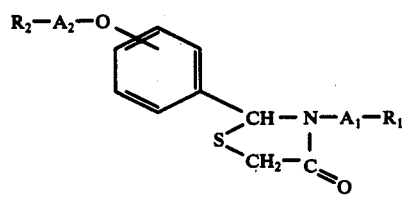

wherein $R_1$ is alkyl, cycloalkyl or aryl; $R_2$ is alkylamino, dialkylamino or a nitrogen containing heterocyclic group; $A_1$ is a saturated bond or an alkylene group having 1 to 4 carbon atoms; and $A_2$ is an alkylene group having 2 to 5 carbon atoms; have anti-inflammatory activity.

11 Claims, No Drawings

4-THIAZOLIDINONE DERIVATIVES

BRIEF DESCRIPTION OF THE INVENTION

Compounds having the formula

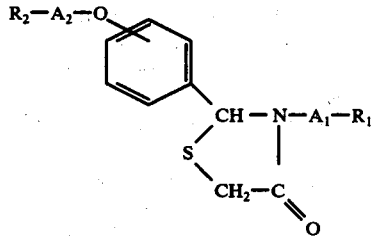

I or a pharmaceutically acceptable salt thereof, have useful antiinflammatory activity. In formula I, and throughout the specification, the symbols are as defined below.

$R_1$ can be alkyl, cycloalkyl or aryl;

$R_2$ can be alkylamino, dialkylamino, or a nitrogen containing heterocyclic group selected from 1-pyrrolidinyl, 1-piperidinyl, 4-morpholinyl, 1-piperazinyl, and 4-alkyl-1-piperazinyl;

$A_1$ can be a saturated bond, or an alkylene group having 1 to 4 carbon atoms; and $A_2$ can be an alkylene group having 2 to 5 carbon atoms.

The term "aryl," as used throughout the specification, refers to phenyl or phenyl substituted with a halogen, alkyl, alkoxy, trifluoromethyl, nitro or amino group.

The terms "alkyl" and "alkoxy," as used throughout the specification, whether by themselves or as part of larger groups, refer to groups having 1 to 6 carbon atoms.

The term "alkylene," as used throughout the specification, refers to a straight or branched chain, divalent, saturated hydrocarbon group.

The term "halogen, " as used throughout the specification, refers to fluorine, chlorine, bromine and iodine; chlorine and bromine are preferred.

The term "cycloalkyl," as used throughout the specification, refers to cycloalkyl groups having 3 to 7 carbon atoms.

DETAILED DESCRIPTION OF THE INVENTION

The compounds of this invention can be prepared using as starting materials a benzaldehyde having the formula

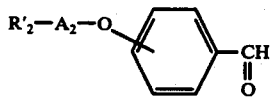

II wherein $R'_2$ is alkylbenzylamino, dialkylamino or a nitrogen containing heterocyclic group, and a primary amine having the formula

         III

Reaction of a benzaldehyde of formula II with an amine of formula III yields the corresponding Schiff base having the formula

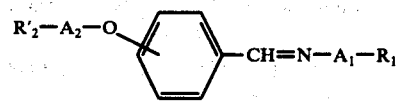

IV

The reaction can be run in an organic solvent, e.g., an aromatic hydrocarbon such as toluene, and will preferably be run at the reflux temperature of the solvent.

The products of formula I, wherein $R_2$ is dialkylamino or a nitrogen containing heterocyclic group, can be prepared by reacting a corresponding compound of formula IV with an alkyl thioglycolate. The reaction can be run in an organic solvent, e.g., an aromatic hydrocarbon such as xylene. While reaction conditions are not critical, the reaction will preferably be run at the reflux temperature of the solvent.

The products of formula I, wherein $R_2$ is alkylamino, can be prepared by first reacting a compound of formula IV, wherein $R'_2$ is alkylbenzylamino, with an alkyl thioglycolate, as described above, to yield an intermediate having the formula

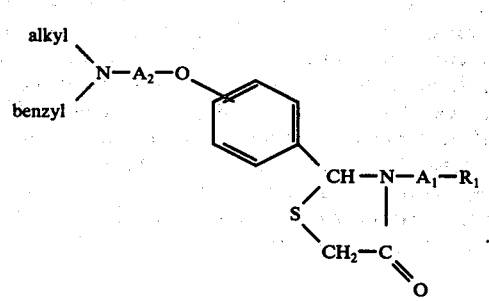

V

Debenzylation of a compound of formula V using the well-known catalytic hydrogenation procedure yields the corresponding product of formula I.

Those products of formula I wherein the $R_1$ group contains an amino substituent are preferably prepared by reduction of the corresponding nitro compound.

The pharmaceutically acceptable salts of the compounds of formula I are readily prepared using procedures well known in the art. Acid addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

The following examples are specific embodiments of this invention.

EXAMPLE 1

2-[2-[3-(Dimethylamino)propoxy]phenyl]-3-(2-phenylethyl)-4-thiazolidinone, oxalate salt (1:1)

A. N-[[2-[3-(Dimethylamino)propoxy]phenyl]methylene]benzeneethanamine

A solution of 32.5 g of 2-(3-dimethylaminopropoxy)benzaldehyde and 18.9 g of phenethylamine in 150 ml of toluene is heated at reflux for 1 hour. After 30 minutes, one mole equivalent of water is collected in a Dean-Stark trap. After cooling to approximately 50° C, the solvent is removed using a rotary evaporator and the oily residue is distilled to give 36.2 g of the title compound, boiling point 165°-167° C at 0.05 mm of Hg.

B. 2-[2-[3-(Dimethylamino)propoxy]phenyl]-3-(2-phenylethyl)-4-thiazolidinone, oxalate salt (1:1)

A solution containing 6.2 g of N-[[2-[3-(dimethylamino)-propoxy]phenyl]methylene]benzeneethanamine and 4.2 g of methyl thioglycolate in 20 ml of xylene is refluxed for 6 hours. Most of the solvent is removed in vacuo and the residual oily product is cooled and dissolved in 50 ml of ether.

The above solution is shaken in a separatory funnel with 50 ml of water containing 3 ml of concentrated hydrochloric acid. The aqueous layer is extracted with two 50 ml portions of ether and treated with an excess of potassium carbonate. The base is extracted into ether, dried, and concentrated to give 7.1 g of an oily residue.

A solution of 6.5 g of the residue in 25 ml of acetonitrile is treated with a solution of 1.5 g of oxalic acid in 25 ml of acetonitrile. Concentration of this solution to approximately one-half volume led to the crystallization of 7.8 g of colorless material, melting point 130°-132° C. Recrystallization from 25 ml of ethanol gives 6.5 g of the title compound, melting point 134°-136° C.

EXAMPLE 2

3-Butyl-2-[2-[3(dimethylamino)propoxy]phenyl]-4-thiazolidinone, oxalate salt (1:1)

A. N-[[2-[3-(Dimethylamino)propoxy]phenyl]methylene]-butanamine 2-(3-Dimethylaminopropoxy)bezaldehyde (32.5 g) is reacted with 11.5 g of n-butylamine in 150 ml of toluene following the procedure described in Example 1, part A, to yield 37.9 g of oil product, boiling point 124°-128° C/0.1-0.2 mm of Hg.

B. 3-Butyl-2-[2-[3-(dimethylamino)propoxy]phenyl]-4-thiazolidinone, oxalate salt (1:1)

N-[[2-[3-(Dimethylamino)propoxy]phenyl]methylene]-butanamine (5.2 g) is reacted with 4.2 g of methyl thioglycolate following the procedure described in Example 1, part B, to yield 6.5 of 3-butyl-2-[2-[3-(dimethylamino)propoxy]phenyl]-4-thiazolidinone as an oil.

A solution of 6.1 g of the oil and 1.7 g of oxalic acid in 25 ml of acetonitrile is diluted to cloudiness with ether. On rubbing, the oxalate salt slowly crystallizes. A further quantity of ether is added to complete the precipitation, and after cooling for about 16 hours, 7.8 g of material is obtained, melting point 67°-69° C. Recrystallization of the material from a mixture of 30 ml of acetonitrile and 100 ml of ether, yields 7.3 g of the title compound, melting point 67°-69° C.

EXAMPLES 3-21

Following the procedure of Example 1, but substituting the compound listed in column I for 2-(3-dimethylaminopropoxy)benzaldehyde and the compound listed in column II for phenethylamine, and omitting the final salt formation, yields the compound listed in column III.

| Column I | Column II | Column III |
| --- | --- | --- |
| 3-(2-diisopropylaminoethoxy)benzaldehyde | n-decylamine | 3-n-decyl-2-[3-[2-(diisopropylamino)-ethoxy]phenyl]-4-thiazolidinone |
| 4-[4-(1-pyrrolidinyl)butoxy]benzaldehyde | isopropylamine | 3-isopropyl-2-[4-[4-(1-pyrrolidinyl)-butoxy]phenyl]-4-thiazolidinone |
| 3-[2-(1-piperidinyl)ethoxy]benzaldehyde | benzylamine | 3-phenylmethyl-2-[3-[2-(1-piperidinyl)-ethoxy]phenyl]-4-thiazolidinone |
| 2-[5-(4-morpholinyl)pentoxy]benzaldehyde | aniline | 2-[2-[5-(4-morpholinyl)pentoxy]phenyl]-3-phenyl-4-thiazolidinone |
| 4-[2-(1-piperazinyl)ethoxy]benzaldehyde | phenethylamine | 3-(2-phenylethyl)-2-[4-[2-(1-piperazinyl)-ethoxy]phenyl]-4-thiazolidinone |
| 2-[3-(4-methyl-1-piperazinyl)propoxy]-benzaldehyde | n-pentylamine | 2-[2-[3-(4-methyl-1-piperazinyl)propoxy]-phenyl]-3-n-pentyl-4-thiazolidinone |
| 3-(3-methylethylaminopropoxy)benzaldehyde | t-butylamine | 3-t-butyl-2-[3-[3-(methylethylamino)propoxy]-phenyl]-4-thiazolidinone |
| 2-(5-dimethylaminopentoxy)benzaldehyde | cyclopropylamine | 3-cyclopropyl-2-[2-[5-(dimethylamino)pentoxy]-phenyl]-4-thiazolidinone |
| 3-(2-dimethylaminoethoxy)benzaldehyde | cyclopropylmethylamine | 3-cyclopropylmethyl-2-[3-[2-(dimethylamino)-ethoxy]phenyl]-4-thiazolidinone |
| 2-(4-dimethylaminobutoxy)benzaldehyde | cyclohexylamine | 3-cyclohexyl-2-[2-[4-(dimethylamino)butoxy]-phenyl]-4-thiazolidinone |
| 4-(2-dimethylaminoethoxy)benzaldehyde | cycloheptylamine | 3-cycloheptyl-2-[4-[2-(dimethylamino)ethoxy]-phenyl]-4-thiazolidinone |
| 2-[2-(1-pyrrolidinyl)ethoxy]benzaldehyde | 3-trifluoromethyl-aniline | 2-[2-[2-(1-pyrrolidinyl)ethoxy]phenyl]-3-(3-trifluoromethylphenyl)-4-thiazolidinone |
| 2-[3-(1-piperidinyl)propoxy]benzaldehyde | 4-fluoroaniline | 3-(4-fluorophenyl)-2-[2-[3-(1-piperidinyl)-propoxy]phenyl]-4-thiazolidinone |
| 3-[4-(4-morpholinyl)butoxy]benzaldehyde | 2-chlorobenzyl-amine | 3-(2-chlorobenzyl)-2-[3-[4-(4-morpholinyl)-butoxy]phenyl]-4-thiazolidinone |
| 3-[5-(1-piperazinyl)pentoxy]benzaldehyde | 3-methylbenzyl-amine | 3-(3-methylbenzyl)-2-[3-[5-(1-piperazinyl)-pentoxy]phenyl]-4-thiazolidinone |
| 4-[2-(4-methyl-1-piperazinyl)ethoxy]-benzaldehyde | 4-methoxyphenethylamine | 3-[2-(4-methoxyphenyl)ethyl]-2-[4-[2-(4-methyl-1-piperazinyl)ethoxy]phenyl]-4-thiazolidinone |
| 2-(3-methylethylaminopropoxy)benzaldehyde | 4-nitrophenethyl-amine | 2-[2-[3-(methylethylamino)propoxy]phenyl]-3-[2-(4-nitrophenyl)ethyl]-4-thiazolidinone |
| 2-(2-methylethylaminoethoxy)benzaldehyde | 3-phenylpropyl-amine | 2-[2-[2-(methylethylamino)ethoxy]phenyl]-3-(3-phenylpropyl)-4-thiazolidinone |
| 3-(2-methylethylaminoethoxy)benzaldehyde | 4-phenylbutyl-amine | 2-[3-[2-(methylethylamino)ethoxy)phenyl]-3-(4-phenylbutyl)-4-thiazolidinone |

EXAMPLE 22

2-[2-[3-(methylethylamino)propoxy]phenyl]-3-[2-[4-aminophenyl)ethyl]-4-thiazolidinone A suspension of 10 parts of 2-[2-[3-(methylethylamino)propoxy]phenyl]-3-[2-(4-nitrophenyl)ethyl]-4-thiazolidinone (see Example 19) in 100 ml of ethanol is treated with 1 part of 5% palladium on carbon and placed under 3 atmospheres of gaseous hydrogen. The mixture is shaken until one equivalent of hydrogen is consumed, filtered and the solvent evaporated under reduced pressure to give the title compound.

EXAMPLE 23

2-[2-[3-(Methylamino)propoxy]phenyl]-3-(2-phenylethyl)-4-thiazolidinone, oxalate salt (1:1)

A. 2-[2-[3-(N-Benzyl-N-methylamino)propoxy]-3-(2-phenylethyl)-4-thiazolidinone, oxalate salt (1:1)

Following the procedure of Example 1, but substituting 2-[3-(N-benzyl-N-methylamino)propoxy]benzaldehyde for 2-(3-dimethylaminopropoxy)benzaldehyde, yields the title compound.

B. 2-[2-[3-(Methylamino)propoxy]phenyl]-3-(2-phenylethyl)-4 -thiazolidinone, oxalate salt (1:1)

A suspension of 10 parts of material from part A in 100 ml of ethanol is treated with 1 part of 5% palladium on carbon and placed under 3 atmospheres of gaseous hydrogen and shaken until one equivalent of hydrogen is consumed. The mixture is filtered to remove the catalyst and the solvent evaporated under reduced pressure to yield the title compound.

What is claimed is:

1. A compound having the formula

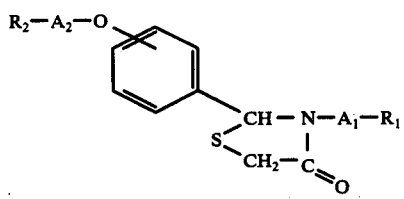

or a pharmaceutically acceptable salt thereof, wherein $R_1$ is alkyl, cycloalkyl or aryl; $R_2$ is alkylamino, dialkylamino, 1-pyrrolidinyl, 1-piperidinyl, 4-morpholinyl, 1-piperazinyl, or 4-alkyl-1-piperazinyl; $A_1$ is a saturated bond or an alkylene group having 1 to 4 carbon atoms; and $A_2$ is an alkylene group having 2 to 5 carbon atoms; wherein the term aryl refers to phenyl or phenyl substituted with a halogen, alkyl, alkoxy, trifluoromethyl, nitro or amino group; alkyl and alkoxy refer to groups having 1 to 6 carbon atoms; and cycloalkyl refers to a group having 3 to 7 carbon atoms.

2. A compound in accordance with claim 1 wherein $R_1$ is alkyl.

3. A compound in accordance with claim 1 wherein $R_1$ is aryl.

4. A compound in accordance with claim 3 wherein $R_1$ is phenyl.

5. A compound in accordance with claim 1 wherein $R_1$ is cycloalkyl.

6. A compound in accordance with claim 1 wherein $R_2$ is alkylamino or dialkylamino.

7. A compound in accordance with claim 1 wherein $R_2$ is 1-pyrrolidinyl, 1-piperidinyl, 4-morpholinyl, 1-piperazinyl, or 4-alkyl-1-piperazinyl.

8. A compound in accordance with claim 6 wherein $R_2$ is dialkylamino.

9. A compound in accordance with claim 8 wherein $R_2$ is dimethylamino.

10. The compound in accordance with claim 1 having the name 2-[2-[3-(dimethylamino)propoxy]phenyl]-3-(2-phenylethyl)-4-thiazolidinone, oxalate salt (1:1).

11. The compound in accordance with claim 1 having the name 3-butyl-2-[2-[3-(dimethylamino)propoxy]phenyl]-4-thiazolidinone, oxalate salt (1:1).

* * * * *